(12) United States Patent
Göke et al.

(10) Patent No.: US 7,265,087 B1
(45) Date of Patent: Sep. 4, 2007

(54) EXENDIN IMPROVES β-CELL RESPONSE IN SUBJECTS WITH IMPAIRED GLUCOSE TOLERANCE

(75) Inventors: Burkhard Göke, Marburg (DE); Maria Byrne, Munster-Hiltrup (DE); Thomas R. Coolidge, Lincoln, NE (US)

(73) Assignee: Amylin Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 09/719,410

(22) PCT Filed: May 7, 1999

(86) PCT No.: PCT/US99/10040

§ 371 (c)(1),
(2), (4) Date: Dec. 12, 2000

(87) PCT Pub. No.: WO99/64061

PCT Pub. Date: Dec. 16, 1999

Related U.S. Application Data (60) Provisional application No. 60/089,044, filed on Jun. 12, 1998.

(51) Int. Cl.
*A61K 38/00* (2006.01)
*A61K 38/28* (2006.01)
*C07K 16/00* (2006.01)

(52) U.S. Cl. .................... 514/12; 514/854; 514/856; 514/929; 514/930; 530/303; 530/308; 530/324

(58) Field of Classification Search .............. 514/12, 514/854, 866, 929, 930; 530/324, 303, 308
See application file for complete search history.

(56) References Cited

U.S. PATENT DOCUMENTS 6,344,180 B1 * 2/2002 Holst et al. ................ 424/9.1

FOREIGN PATENT DOCUMENTS

| WO | WO97/46584 |   | 12/1997 |
|----|------------|---|---------|
| WO | WO98/08531 | * | 3/1998  |
| WO | WO98 08531 A |  | 3/1998  |

OTHER PUBLICATIONS

Rachman et al., Diabetologia, vol. 40, pp. 205-211, 1997.*
Rachman J et al: "Near-normalisation of diurnal goucose concentrations by continuous administration of glucagon-like peptide-1 (GLP-1) in subjects with NIDDM." DIABETOLOGIA, (Feb. 1997) 40 (2) 205-11., XP002122529.

Cavaghan M K et al: "Treatment with the oral antidiabetic agent troglitazone imprves beta cell responses to glucose in subjects with impaired glucose tolerance." Journal Of Clincal Investigation, (Aug. 1, 1997) 100 (3) 530-7., XP002122530 the whole document.
Byrne M M Et Al: "Glucagon—like peptide 1 improves the ability of the beta—cell to sense and respond to glucose in subjects with impaired glucose tolerance." DIABETEs, (Aug. 1998) 47 (8) 1259-65., XP002122530 the whole document.
D'Alessio, D. A., et al., "Elimination of the Action of Glucagon-Like Peptide-1 Causes an Impairment of Glucose Tolerance After Nutrient Ingestion by Healthy Baboons" *Journal Of Clincal Investigation*, (Jan. 1996) 97 (1) 133-138.
Ritzel, U., et al., "A Synthetic Glucagon-Like Peptide-1 Analog With Improved Plasma Stability" *Journal Of Endocrinology*,(Oct. 1998) Bristol, GB, 159 (1) 93-102.
Schirra, J., et al., "Exendin (9-39) Amide is an Antagoinist of Glucagon-Like Peptide-1 (7-36) Amide in Humans" *Journal Of Clincal Investigation* (Apr. 1998) 101 (7) 1421-1430.
Byrne et al., "Glucagon-Like Peptide-1 Improves the Ability of the β-Cell to Sense and Respond to Glucose in Subjects with Impaired Glucose Tolerance", *Diabetes*, vol. 46, Supplement (1), p. 33A, Abstract 0127 (1997).
Byrne et al., "GLP-1 Improves First Phase Insulin Secretion without Altering Insulin Sensitivity in Subjects with Impaired Glucose Tolerance", *Diabetes*, vol. 47, Supplement (1), p. A192, Abstract 0744 (1998).
Byrne & Göke, "Human Studies with Glucagon-like-peptide-1: Potential of the Gut Hormone for Clinical Use", *Diabetic Medicine*, vol. 13, pp. 854-860 (1996).
Wang et al., "Glucagon-like Peptide-1 Can Reverse the Age-related Decline in Glucose Tolerance in Rats", *The Journal of Clincal Investigation*, vol. 99, No. 22, pp. 2883-2889 (1997).
European Search Report published Jan. 12, 2005 in European Pat. Appl. No. 04075402.0.
Byrne—GLP-1 Improves First Phase Insulin Secretion without Altering Insulin Sensitivity in Subject with Impaired Glucose Tolerance; Diabetes; vol. 47; Abstract 0744, p. A192, (May-1998).
Byrne-Human Studies with Glucagon-like-Peptide-1: Potential of the Gut Hormone for Clincal Use; Diabetes Medicine, vol. 13; Issue 10; pp. 854-860 (Oct. 1996).

* cited by examiner

*Primary Examiner*—Cecilia J. Tsang
*Assistant Examiner*—Abdel A Mohamed

(57) ABSTRACT

A composition for the treatment of impaired glucose tolerance (IGT) including a compound which binds to a receptor for glucagon-like peptide-1, and a pharmaceutical carrier. The amount of the compound present is an effective amount to improve pancreatic β-cell sensitivity to blood glucose levels in a human with IGT. Also, a method for improving the pattern of insulin secretory responses in a human with IGT by administering to the human a composition comprising a compound which binds to a receptor for glucagon-like peptide-1 and a pharmaceutical carrier.

14 Claims, 9 Drawing Sheets

SEQUENCE LISTING

```
<160> NUMBER OF SEQ ID NOS: 13

<210> SEQ ID NO 1
<211> LENGTH: 37
<212> TYPE: PRT
<213> ORGANISM: mammalian

<400> SEQUENCE: 1

His Asp Glu Phe Glu Arg His Ala Glu Gly Thr Phe Thr Ser Asp Val
 1               5                  10                  15

Ser Ser Tyr Leu Glu Gly Gln Ala Ala Lys Glu Phe Ile Ala Trp Leu
            20                  25                  30

Val Lys Gly Arg Gly
        35

<210> SEQ ID NO 2
<211> LENGTH: 36
<212> TYPE: PRT
<213> ORGANISM: mammalian
```

-continued

```
<400> SEQUENCE: 2

His Asp Glu Phe Glu Arg His Ala Glu Gly Thr Phe Thr Ser Asp Val
 1               5                  10                  15

Ser Ser Tyr Leu Glu Gly Gln Ala Ala Lys Glu Phe Ile Ala Trp Leu
             20                  25                  30

Val Lys Gly Arg
         35

<210> SEQ ID NO 3
<211> LENGTH: 31
<212> TYPE: PRT
<213> ORGANISM: mammalian

<400> SEQUENCE: 3

His Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg Gly
             20                  25                  30

<210> SEQ ID NO 4
<211> LENGTH: 30
<212> TYPE: PRT
<213> ORGANISM: mammalian

<400> SEQUENCE: 4

His Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg
             20                  25                  30

<210> SEQ ID NO 5
<211> LENGTH: 29
<212> TYPE: PRT
<213> ORGANISM: mammalian

<400> SEQUENCE: 5

Glu Gly Thr Phe Thr Ser Asp Val Ser Ser Tyr Leu Glu Gly Gln Ala
 1               5                  10                  15

Ala Lys Glu Phe Ile Ala Trp Leu Val Lys Gly Arg Gly
             20                  25

<210> SEQ ID NO 6
<211> LENGTH: 28
<212> TYPE: PRT
<213> ORGANISM: mammalian

<400> SEQUENCE: 6

Glu Gly Thr Phe Thr Ser Asp Val Ser Ser Tyr Leu Glu Gly Gln Ala
 1               5                  10                  15

Ala Lys Glu Phe Ile Ala Trp Leu Val Lys Gly Arg
             20                  25

<210> SEQ ID NO 7
<211> LENGTH: 39
<212> TYPE: PRT
<213> ORGANISM: Heloderma suspectum

<400> SEQUENCE: 7

His Ser Asp Gly Thr Phe Thr Ser Asp Leu Ser Lys Gln Met Glu Glu
 1               5                  10                  15
```

```
Glu Ala Val Arg Leu Phe Ile Glu Trp Leu Lys Asn Gly Gly Pro Ser
            20                  25                  30

Ser Gly Ala Pro Pro Ser
        35

<210> SEQ ID NO 8
<211> LENGTH: 31
<212> TYPE: PRT
<213> ORGANISM: Heloderma suspectum

<400> SEQUENCE: 8

Asp Leu Ser Lys Gln Met Glu Glu Ala Val Arg Leu Phe Ile Glu
1               5                   10                  15

Trp Leu Lys Asn Gly Gly Pro Ser Ser Gly Ala Pro Pro Ser
            20                  25                  30

<210> SEQ ID NO 9
<211> LENGTH: 39
<212> TYPE: PRT
<213> ORGANISM: Heloderma suspectum

<400> SEQUENCE: 9

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser
        35

<210> SEQ ID NO 10
<211> LENGTH: 38
<212> TYPE: PRT
<213> ORGANISM: Heloderma suspectum

<400> SEQUENCE: 10

His Ser Asp Ala Thr Phe Thr Ala Glu Tyr Ser Lys Leu Leu Ala Lys
1               5                   10                  15

Leu Ala Leu Gln Lys Tyr Leu Glu Ser Ile Leu Gly Ser Ser Thr Ser
            20                  25                  30

Pro Arg Pro Pro Ser Ser
        35

<210> SEQ ID NO 11
<211> LENGTH: 37
<212> TYPE: PRT
<213> ORGANISM: Heloderma suspectum

<400> SEQUENCE: 11

His Ser Asp Ala Thr Phe Thr Ala Glu Tyr Ser Lys Leu Leu Ala Lys
1               5                   10                  15

Leu Ala Leu Gln Lys Tyr Leu Glu Ser Ile Leu Gly Ser Ser Thr Ser
            20                  25                  30

Pro Arg Pro Pro Ser
        35

<210> SEQ ID NO 12
<211> LENGTH: 35
<212> TYPE: PRT
<213> ORGANISM: Heloderma suspectum

<400> SEQUENCE: 12
```

```
His Ser Asp Ala Ile Phe Thr Glu Glu Tyr Ser Lys Leu Leu Ala Lys
 1               5                  10                  15

Leu Ala Leu Gln Lys Tyr Leu Ala Ser Ile Leu Gly Ser Arg Thr Ser
             20                  25                  30

Pro Pro Pro
         35

<210> SEQ ID NO 13
<211> LENGTH: 35
<212> TYPE: PRT
<213> ORGANISM: Heloderma suspectum

<400> SEQUENCE: 13

His Ser Asp Ala Ile Phe Thr Gln Gln Tyr Ser Lys Leu Leu Ala Lys
 1               5                  10                  15

Leu Ala Leu Gln Lys Tyr Leu Ala Ser Ile Leu Gly Ser Arg Thr Ser
             20                  25                  30

Pro Pro Pro
         35
```

EXENDIN IMPROVES β-CELL RESPONSE IN SUBJECTS WITH IMPAIRED GLUCOSE TOLERANCE

CROSS-REFERENCE TO RELATED APPLICATIONS

This application is a continuation-in-part of and claims the benefit of the filing date of U.S. Provisional Application No. 60/089,044 filed Jun. 12, 1998.

BACKGROUND OF THE INVENTION

Impaired glucose tolerance (IGT) is common in the U.S. population. The prevalence of impaired glucose tolerance increases from 11% in the general population aged 20-74 years to 24% in those 40-75 years of age with a family history of diabetes and a body weight greater than 120% of normal. Subjects with impaired glucose tolerance are at high risk for the development of cardiovascular disease as well as non-insulin dependent diabetes mellitus (NIDDM), also known as Type 2 diabetes.

Impaired glucose tolerance is characterized by early subtle defects in pancreatic β-cell function, accompanied by insulin resistance. These early defects include an impaired ability of the β-cell to sense and respond to small changes in plasma glucose concentrations with appropriate levels of insulin secretion, and a mild shift to the right of the glucose insulin secretion dose-response curve. The glucose sensing and fast insulin secretion response abilities of the β-cell are lost very early in the course of IGT when 2-hour glucose levels are minimally elevated. The deterioration of glucose control in IGT with time is predominantly due to progressive impairment of β-cell function. This leads, in many cases, to deteriorating conditions of hyperinsulinemia, obesity, and cardiovascular disease, sometimes known as Syndrome X. In many cases advanced IGT conditions lead to definitive loss of glucose control and the deleterious onset of NIDDM.

As indicated, the condition of IGT carries serious health risks. The IGT patient is often obese and has high plasma levels of insulin, which are often toxic. These high insulin levels result generally from the continually increased inability of muscle, other tissue and fat cells to utilize insulin to effect the uptake of glucose from blood plasma. The IGT condition gives rise to increased risks for a whole range of cardiovascular diseases.

Glucagon-like peptide-1 (GLP-1), a natural enteric peptide, is secreted from the L-cells of the gut, and acts as an incretin hormone stimulating pancreatic β-cells to secrete insulin in a glucose dependent manner. Its therapeutic potential in NIDDM has been previously demonstrated, in that exogenous infusion of pharmacological doses of GLP-1 generally reduced plasma glucose levels. However, GLP-1 did not significantly improve β-cell function in NIDDM. Nathan DM, Schreiber E, Fogel H, Mojsov S, Habener J F. Insulinotropic action of glucagon-like peptide-1 (7-37) in diabetic and nondiabetic subjects. *Diabetes Care* 15:270-276, 1992; Gutniak M, Ørskov C, Holst J J, Ahrén B, Efendric S. Antidiabetogenic effects of glucagon-like peptide-1 (7-36) amide in normal subjects and patients with diabetes mellitus. *N Engl J Med* 326:1316-1322, 1992; Nauck M A, Kleine N, Orskov C, Holst J J, Willms B, Creutzfeldt W. Normalization of fasting hyperglycemia by exogenous glucagon-like peptide-1 (7-36 amide) in type II (non-insulin-dependent) diabetic patients. *Diabetologia* 36:741-744, 1993; Gutniak M K, Linde B, Holst J J, Efendie S. Subcutaneous injection of the incretin hormone glucagon-like peptide-1 abolishes postprandial glycemia NIDDM. *Diabetes Care* 17:1039-1044, 1994; Rachman J, Gribble F M, Barrow B A, Levy J C, Buchanan K D, Turner R C. Normalization of insulin responses to glucose by overnight infusion of glucagon-like peptide 1 (7-36) amide in patients with NIDDM. *Diabetes* 45:1524-1530, 1996; Rachman J, Barrow B A, Levy J C, Turner R C. Near-normalization of diurnal glucose concentrations by continuous administration of glucagon-like peptide-1 (GLP-1) in subjects with NIDDM, *Diabetologia* 40:205-211, 1997.

The IGT condition is not currently treatable. It is, however, a recognizable disease condition associated with serious health risks. In general, the IGT condition progressively deteriorates in terms of its symptoms and often leads to loss of plasma glucose control which constitutes type 2 diabetes. There is a need for a therapy.

Numerous studies over the past several years have demonstrated that the application of GLP-1 in cases of NIDDM lowers glucose and insulin levels in the blood, and hence should be a promising therapy for that disease. However, no studies to date have shown that GLP-1 has a potential to correct the loss of the ability of β-cells to sense and quickly respond with the secretion of insulin when blood glucose increases. It is this deterioration in the ability to respond and to closely link the sensing of increases in blood glucose to insulin secretion from the β-cells which is the principal cause of the IGT condition. In previous studies the application of GLP-1 to NIDDM subjects demonstrated an ability to normalize fasting plasma glucose and to stimulate cumulative β-cell insulin secretion. However, GLP-1 infused overnight in NIDDM subjects did not improve glucose responses to meals the next day. When GLP-1 was infused for 19 hours, overnight and during three standard meals in subjects with NIDDM, plasma glucose levels were reduced, but the impaired post-prandial β-cell function was only slightly improved.

β-cell responses to prolonged infusion of GLP-1 have not been previously studied in subjects with IGT and, while there has been no indication that the result would be different than with GLP-1 infusions in NIDDMs, detailed studies of the effect of GLP-1 on β-cell responses to small increases and decreases in plasma glucose concentrations have not been heretofore performed.

Accordingly, a method to arrest the progression of IGT and restore normal glucose metabolism conditions is needed.

It is therefore an object of the present invention to provide a method of restoring or improving β-cell function and sensitivity, and thus insulin secretion patterns, in response to plasma glucose levels in a host having impaired glucose tolerance.

A further object of the invention is to provide a method to delay or prevent the deterioration of β-cell function which is responsible for the progression of impaired glucose tolerance into the loss of control over plasma glucose which characterizes the onset of NIDDM.

A yet further object of the invention is to ameliorate cardiovascular disease effects of IGT, thereby decreasing cardiovascular and stroke risks.

The method of accomplishing these and other objects will be apparent from the following detailed description.

SUMMARY OF THE INVENTION

The inventors have discovered that the application of GLP-1 in subjects with impaired glucose tolerance reestablishes the tightly coordinated response of insulin secretion to increases in plasma glucose levels, thereby restoring the insulin secretion response patterns from the β-cell to plasma glucose level increases which are characteristic of normal subjects without IGT.

Thus the present invention is directed to a method of treating a host having impaired glucose tolerance and insulin resistance with GLP-1 in an amount effective to restore, improve or normalize β-cell sensitivity and function and insulin secretion patterns in that host. The invention is also directed to a method of reducing plasma insulin level in persons with IGT and concurrently reducing the condition of insulin resistance and its concomitant condition of cardiovascular disease.

In carrying out the examples described herein, the inventors have surprisingly observed that the application of GLP-1 in subjects with IGT, in contrast to random and uncoordinated insulin response characteristically encountered in IGT subjects, dramatically recreates sensitive, quick and coordinated insulin secretions from the β-cells in response to discreet pulsatile increases in plasma glucose similar to insulin secretion patterns found in normal patients.

BRIEF DESCRIPTION OF THE DRAWINGS

FIG. 1 shows the glucose, insulin and GLP-1 responses to oral administration of 75 mg of glucose in five subjects with impaired glucose tolerance (IGT •) and five subjects with non-insulin dependent diabetes mellitus (NIDDM □).

FIG. 2 provides a comparison of mean insulin secretion rates (ISR) and mean glucose concentrations in each subject during glucose infusion with saline infusion (O) or GLP-1 infusion (•).

FIG. 3 provides profiles of the glucose, insulin secretion rates (ISR) and insulin concentrations in two subjects with IGT, subjects D01 and D02.

FIG. 4 provides a comparison of glucose levels, insulin secretion rates (ISR) and insulin levels in two subjects with NIDDM, subjects D07 and D09.

FIGS. 6A-6D provide a comparison of normalized spectral power during saline infusion and during GLP-1 infusion.

DETAILED DESCRIPTION OF THE INVENTION

The inventors have discovered that the administration of GLP-1 in subjects with impaired glucose tolerance (IGT) restored or improved pancreatic β-cell function and the ability of β-cells to respond quickly in secreting insulin in a coordinated manner in response to small increases or changes in plasma glucose concentrations, i.e. pulsatile secretions of insulin, similar to insulin secretion patterns found in subjects without IGT. This pattern of insulin secretion is not restored in subjects who have already developed NIDDM, which is characterized by loss of plasma glucose control.

β-cell function is quantified by normalized spectral power. Spectral power measures β-cell function which does not rely on adjustment for insulin sensitivity. The inventors have found that in subjects with IGT, GLP-1 improves spectral power into a normal range. The spectral power profiles indicated that the entrainment or close coordination of plasma glucose and insulin secretion oscillations were restored to normal levels in IGT subjects after administration of GLP-1. This improvement in the oscillatory pattern of insulin secretion is important for the maintenance of normal glucose homeostasis. For example, it has been shown that insulin infusions that mimic the ultradian oscillations within a period of 120 minutes are more effective than constant infusions of insulin in the reduction of plasma glucose concentrations.

The present invention provides a composition comprising a compound which binds to a receptor for glucagon-like peptide-1 and is effective in improving the ability of β-cells to sense and respond to small changes in plasma glucose concentrations in subjects with IGT. In one embodiment, the receptor-binding compound is glucagon-like peptide-1. In another embodiment, the receptor-binding compound is a variant peptide in which the combination of the substitutions, deletions and variants does not differ by more than ten amino acids from glucagon-like peptide-1. The receptor-binding compound can further comprise a polynucleotide or an agent which activates the release of GLP-1, a molecule which activates the GLP-1 receptor, or a GLP-1 receptor binding compound comprising a chemically constructed molecule, peptide analogs, or agonists of GLP-1.

The inventors have discovered that the administration of human GLP-1 enhanced or restored entrainment of insulin secretion responses to small changes or increases in plasma glucose. Accordingly, the composition of the present invention is useful in therapeutic treatment for normalizing impaired glucose tolerance.

The inventors have demonstrated herein that a low dose infusion of GLP-1 can improve the function of the β-cells to secrete insulin in response to increases in plasma glucose levels. Thus, GLP-1 can also be used to improve the preservation of β-cell function in subjects with IGT. Administration of GLP-1 also regulates or normalizes insulin secretion patterns which will result in overall reduction of plasma insulin in IGT. This normalization in turn will reduce the condition of insulin resistance.

The term "GLP-1", or glucagon-like peptide, includes GLP-1 mimetics, and as used in the context of the present invention can be comprised of glucagon-like peptides and related peptides and analogs of glucagon-like peptide-1 that bind to a glucagon-like peptide-1 (GLP-1) receptor protein such as the GLP-1 (7-36) amide receptor protein and has a corresponding biological effect on insulin secretion as GLP-1 (7-36) amide, which is a native, biologically active form of GLP-1. See Göke, B and Byrne, M, *Diabetic Medicine.* 1996, 13:854-860. The GLP-1 receptors are cell-surface proteins found, for example, on insulin-producing pancreatic β-cells. Glucagon-like peptides and analogs will include species having insulinotropic activity and that are agonists of, i.e. activate, the GLP-1 receptor molecule and its second messenger activity on, inter alia, insulin producing β-cells. Agonists of glucagon-like peptide that exhibit activity through this receptor have been described: EP 0708179A2; Hjorth, S. A. et al., *J. Biol. Chem.* 269 (48): 30121-30124 (1994); Siegel, E. G. et al. Amer. Diabetes Assoc. 57th Scientific Sessions, Boston (1997); Hareter, A. et al. Amer. Diabetes Assoc. 57th Scientific Sessions, Boston (1997); Adelhorst, K. et al. *J. Biol. Chem.* 269(9):6275-6278 (1994); Deacon C. F. et al. 16th International Diabetes Federation Congress Abstracts, *Diabetologia Supplement* (1997); Irwin, D. M. et al., *Proc. Natl. Acad. Sci. USA.* 94:7915-7920 (1997); Mosjov, S. *Int. J. Peptide Protein Res.* 40:333-343 (1992). Glucagon-like molecules include polynucleotides that express agonists of GLP-1, i.e. activators of the GLP-1 receptor molecule and its secondary messenger activity found on, inter alia, insulin-producing β-cells. GLP-1 mimetics that also are agonists of β-cells include, for example, chemical compounds specifically designed to activate the GLP-1 receptor. Glucagon-like peptide-1 antagonists are also known, for example see e.g. Watanabe, Y. et al., *J. Endocrinol.* 140(1):45-52 (1994), and include exendin (9-39) amine, an exendin analog, which is a potent antagonist of GLP-1 receptors (see, e.g. WO97/46584). Recent publications disclose Black Widow GLP-1 and Ser$^2$ GLP-1, see G. G. Holz, J. F. Hakner/*Comparative Biochemistry and Physiology*, Part B 121 (1998) 177-184 and Ritzel, et al., *A synthetic glucagon-like peptide-1 analog with improved plasma stability*, J. Endocrinol 1998 October; 159(1):93-102.

Further embodiments include chemically synthesized glucagon-like polypeptides as well as any polypeptides or fragments thereof which are substantially homologous. "Substantially homologous," which can refer both to nucleic acid and amino acid sequences, means that a particular subject sequence, for example, a mutant sequence, varies from a reference sequence by one or more substitutions, deletions, or additions, the net effect of which does not result in an adverse functional dissimilarity between reference and subject sequences. For purposes of the present invention, sequences having greater than 50 percent homology, and preferably greater than 90 percent homology, equivalent biological activity in enhancing β-cell responses to plasma glucose levels, and equivalent expression characteristics are considered substantially homologous. For purposes of determining homology, truncation of the mature sequence should be disregarded. Sequences having lesser degrees of homology, comparable bioactivity, and equivalent expression characteristics are considered equivalents.

Mammalian GLP peptides and glucagon are encoded by the same gene. In the ileum the phenotype is processed into two major classes of GLP peptide hormones, namely GLP-1 and GLP-2. There are four GLP-1 related peptides known which are processed from the phenotypic peptides. GLP-1 (1-37) has the sequence His Asp Glu Phe Glu Arg His Ala Glu Gly Thr Phe Thr Ser Asp Val Ser Ser Tyr Leu Glu Gly Gln Ala Ala Lys Glu Phe Ile Ala Trp Leu Val Lys Gly Arg Gly SEQ ID NO:1. GLP-1 (1-37) is amidated by post-translational processing to yield GLP-1 (1-36) NH$_2$ which has the sequence His Asp Glu Phe Glu Arg His Ala Glu Gly Thr Phe Thr Ser Asp Val Ser Ser Tyr Leu Glu Gly Gln Ala Ala Lys Glu Phe Ile Ala Trp Leu Val Lys Gly Arg (NH$_2$) SEQ ID NO:2; or is enzymatically processed to yield GLP-1 (7-37) which has the sequence His Ala Glu Gly Thr Phe Thr Ser Asp Val Ser Ser Tyr Leu Glu Gly Gln Ala Ala Lys Glu Phe Ile Ala Trp Leu Val Lys Gly Arg Gly SEQ ID NO:3. GLP-1 (7-37) can also be amidated to yield GLP-1 (7-36) amide which is the natural form of the GLP-1 molecule, and which has the sequence His Ala Glu Gly Thr Phe Thr Ser Asp Val Ser Ser Tyr Leu Glu Gly Gln Ala Ala Lys Glu Phe Ile Ala Trp Leu Val Lys Gly Arg (NH$_2$) SEQ ID NO:4 and in the natural form of the GLP-1 molecule.

Intestinal L cells secrete GLP-1 (7-37) SEQ ID NO:3 and GLP-1 (7-36)NH$_2$ SEQ ID NO:4 in a ratio of 1 to 5, respectively. These truncated forms of GLP-1 have short half-lives in situ, i.e., less than 10 minutes, and are inactivated by an aminodipeptidase IV to yield Glu Gly Thr Phe Thr Ser Asp Val Ser Ser Tyr Leu Glu Gly Gln Ala Ala Lys Glu Phe Ile Ala Trp Leu Val Lys Gly Arg Gly SEQ ID NO:5; and Glu Gly Thr Phe Thr Ser Asp Val Ser Ser Tyr Leu Glu Gly Gln Ala Ala Lys Glu Phe Ile Ala Trp Leu Val Lys Gly Arg (NH$_2$) SEQ ID NO:6, respectively. The peptides Glu Gly Thr Phe Thr Ser Asp Val Ser Ser Tyr Leu Glu Gly Gln Ala Ala Lys Glu Phe Ile Ala Trp Leu Val Lys Gly Arg Gly SEQ ID NO:5 and Glu Gly Thr Phe Thr Ser Asp Val Ser Ser Tyr Leu Glu Gly Gln Ala Ala Lys Glu Phe Ile Ala Trp Leu Val Lys Gly Arg (NH$_2$) SEQ ID NO:6, have been speculated to affect hepatic glucose production, but do not stimulate the production or release of insulin from the pancreas.

There are six peptides in Gila monster venoms that are homologous to GLP-1. Their sequences are compared to the sequence of GLP-1 in Table 1.

TABLE 1

| | |
|---|---|
| a. | HAEGTFTSDVSSYLEGQAAKEFIAWLVKGR NH$_2$ |
| b. | HSDGTFTSDLSKQMEEEAVRLFIEWLKNGGPSSGAPPPS NH$_2$ |
| c. | DLSKQMEEEAVRLFIEWLKNGGPSSGAPPPS NH$_2$ |
| d. | HGEGTFTSDLSKQMEEEAVRLFIEWLKNGGPSSGAPPPS NH$_2$ |
| e. | HSDATFTAEYSKLLAKLALQKYLESILGSSTSPRPPSS |
| f. | HSDATFTAEYSKLLAKLALQKYLESILGSSTSPRPPS |
| g. | HSDAIFTEEYSKLLAKLALQKYLASILGSRTSPPP NH$_2$ |
| h. | HSDAIFTQQYSKLLAKLALQKYLASILGSRTSPPP NH$_2$ | a. = GLP-1 SEQ ID NO:4
b. = Exendin 3 SEQ ID NO:7
c. = Exendin 4(9-39)(NH$_2$) SEQ ID NO:8
d. = Exendin 4 SEQ ID NO:9
e. = Helospectin I SEQ ID NO:10
f. = Helospectin II SEQ ID NO:11
g. = Helodermin SEQ ID NO:12
h. = Q$^8$, Q$^9$ Helodermin SEQ ID NO:13

The major homologies as indicated by the outlined areas in Table 1 are: peptides c and h are derived from d and g, respectively. All 6 naturally occurring peptides (a, b, d, e, f and g) are homologous in positions 1, 7, 11 and 18. GLP-1 and exendins 3 and 4 (a, b and d) are further homologous in positions 4, 5, 6, 8, 9, 15, 22, 23, 25, 26 and 29. In position 2, A, S and G are structurally similar. In position 3, residues D and E (Asp and Glu) are structurally similar. In positions 22 and 23 F (Phe) and I (Ile) are structurally similar to Y (Tyr) and L (Leu), respectively. Likewise, in position 26 L and I are structurally equivalent.

Thus, of the 30 residues of GLP-1, exendins 3 and 4 are identical in 15 positions and equivalent in 5 additional positions. The only positions where radical structural changes are evident are at residues 16, 17, 19, 21, 24, 27, 28 and 30. Exendins also have 9 extra residues at the carboxyl terminus.

The GLP-1 like peptides can be made by solid state chemical peptide synthesis. GLP-1 can also be made by conventional recombinant techniques using standard procedures described in, for example, Sambrook and Maniaitis. "Recombinant", as used herein, means that a protein is derived from recombinant (e.g., microbial or mammalian) expression systems which have been genetically modified to contain an expression gene for GLP-1 or its biologically active analogues.

The GLP-1 like peptides can be recovered and purified from recombinant cell cultures by methods including, but not limited to, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography (HPLC) can be employed for final purification steps.

The polypeptides of the present invention may be a naturally purified product, or a product of chemical synthetic procedures, or produced by recombinant techniques from prokaryotic or eukaryotic hosts (for example by bacteria, yeast, higher plant, insect and mammalian cells in culture or in vivo). Depending on the host employed in a recombinant production procedure, the polypeptides of the present invention are generally non-glycosylated, but may be glycosylated.

GLP-1 activity can be determined by standard methods, in general, by receptor-binding activity screening procedures which involve providing appropriate cells that express the GLP-1 receptor on their surface, for example, insulinoma cell lines such as RINmSF cells or INS-1 cells. See also Mosjov, S. (1992) and EP0708170A2. In addition to measuring specific binding of tracer to membrane using radioimmunoassay methods, cAMP activity or glucose dependent insulin production can also be measured. In one method, a polynucleotide encoding the receptor of the present invention is employed to transfect cells to thereby express the GLP-1 receptor protein. Thus, for example, these methods may be employed for screening for a receptor agonist by contacting such cells with compounds to be screened and determining whether such compounds generate a signal, i.e. activate the receptor.

Polyclonal and monoclonal antibodies can be utilized to detect purify and identify GLP-1 like peptides for use in the methods described herein. Antibodies such as ABGA1178 detect intact unspliced GLP-1 (1-37) or N-terminally-truncated GLP-1 (7-37) or (7-36) amide. Other antibodies detect on the very end of the C-terminus of the precursor molecule, a procedure which allows by subtraction to calculate the amount of biologically active truncated peptide, i.e. GLP-1 (7-37) or (7-36) amide (Orskov et al. Diabetes, 1993, 42:658-661; Orskov et al. *J. Clin. Invest.* 1991, 87:415-423).

Other screening techniques include the use of cells which express the GLP-1 receptor, for example, transfected CHO cells, in a system which measures extracellular pH or ionic changes caused by receptor activation. For example, potential agonists may be contacted with a cell which expresses the GLP-1 protein receptor and a second messenger response, e.g. signal transduction or ionic or pH changes, may be measured to determine whether the potential agonist is effective.

The glucagon-like peptide-1 receptor binding proteins of the present invention may be used in combination with a suitable pharmaceutical carrier. Such compositions comprise a therapeutically effective amount of the polypeptide, and a pharmaceutically acceptable carrier or excipient. Such a carrier includes, but is not limited, to saline, buffered saline, dextrose, water, glycerol, ethanol, lactose, phosphate, mannitol, arginine, trehalose and combinations thereof. The formulations should suit the mode of administration and are readily ascertained by those of skill in the art. The GLP-1 peptide may also be used in combination with agents known in the art that enhance the half-life in vivo of the peptide in order to enhance or prolong the biological activity of the peptide. For example, a molecule or chemical moiety may be covalently linked to the composition of the present invention before administration thereof. Alternatively, the enhancing agent may be administered concurrently with the composition. Still further, the agent may comprise a molecule that is known to inhibit the enzymatic degradation of GLP-1 like peptides may be administered concurrently with or after administration of the GLP-1 peptide composition. Such a molecule may be administered, for example, orally or by injection.

GLP-1 can be administered intravenously or subcutaneously, and can be administered continuously or by bolus injection. Total administration can be together with, before or after glucose injection or infusion. The following doses can be used: For continuous infusion by intravenous (I.V.) 0.1 pmol/kg/min to 10 pmol/kg/min and by subcutaneous (S.C.) 0.1 pmol/kg/min to 75 pmol/kg/min, and for single injection (bolus) by I.V. 0.005 nmol/kg to 20 nmol/kg and S.C. 0.1 nmol/kg to 100 nmol/kg.

The preferred method of administration of the GLP-1 peptide is through a continuous application. However, GLP-1 can be delivered by subcutaneous, intramuscular, interperitoneal, injected depot with sustained release, deep lung insufflation with sustained release as well as by intravenous, buccal, patch or other delivery method.

The effective treatment of IGT also decreases the risk of cardiovascular and cerebrovascular events. It can therefore be provided as a preventative to patients of known high risk for such events.

The following examples further illustrate an aspect of the present invention. However, these examples should in no way be taken as a limitation of the teachings or disclosure of the present invention to the exemplary limits in terms of scope.

EXAMPLES

The studies described herein were performed in 10 subjects who were divided into two groups on the basis of their plasma glucose response to an oral glucose tolerance test using the criteria of the World Health Organization to define the degree of glucose tolerance. Five subjects had IGT, and five subjects had NIDDM. The gender, age, body mass index (BMI), basal levels of fasting glucose, 2 hour glucose, fasting insulin, and HBA1c for each subject are presented in Table 2. Diabetic subjects were older than those with IGT, but the groups were matched for by BMI. Mean fasting glucose levels and glycosylated hemoglobin concentrations were lower in the IGT group compared to subjects with NIDDM. Fasting insulin levels did not differ between the groups.

TABLE 2

Baseline clinical parameters or IGT and NIDDM subjects

| ID | Sex | Age | BMI | Fasting glucose (mM) | 2 hr glucose (mM) | Fasting Insulin (pmol/L) | Glyco-hemoglobin |
|---|---|---|---|---|---|---|---|
| IGT | | | | | | | |
| D01 | M | 50 | 25.7 | 5.78 | 8.99 | 54.84 | 5.8 |
| D02 | F | 52 | 26.8 | 5.94 | 10.52 | 79.80 | 5.7 |
| D03 | M | 49 | 32.2 | 5.73 | 9.45 | 73.68 | 6.3 |
| D04 | M | 42 | 30.6 | 5.99 | 9.89 | 35.52 | 5.9 |
| D05 | M | 46 | 38.2 | 6.14 | 11.06 | 92.88 | 6.5 |
| Mean ± SE | | 47.8 ± 1.7 | 30.7 ± 2.2 | 5.92 ± 0.07 | 9.98 ± 0.37 | 67.3 ± 10.0 | 6.04 ± 0.15 |
| NIDDM | | | | | | | |
| D06 | M | 53 | 26.4 | 8.81 | 16.27 | 30.78 | 6.7 |
| D07 | M | 61 | 27.9 | 6.87 | 11.28 | 81.60 | 7.2 |
| D08 | M | 60 | 34.2 | 7.66 | 15.05 | 37.44 | 5.9 |
| D09 | M | 53 | 27.8 | 6.86 | 18.66 | 47.88 | 7.7 |
| D10 | M | 66 | 23.9 | 8.34 | 12.9 | 24.84 | 8.1 |
| Mean ± SE | | 58.6 ± 2.5 | 28.1 ± 1.7 | 7.71 ± 0.39 | 14.83 ± 1.29 | 44.5 ± 10.0 | 7.12 ± 0.39 |
| P value | | P < 0.009 | P = 0.36 | P < 0.002 | P < 0.007 | P = 0.15 | P < 0.04 |

Plasma glucose levels were measured by the glucose oxidase technique (YSI, 1500 G, Schlag Company, Bergisch-Gladbach, Germany). The coefficient of variation of this method was <2%. Plasma insulin was measured by the Abbott IMx Microparticle Enzyme Immunoassay. The average intraassay coefficient of variation was 5%. Plasma C-peptide was measured as previously described in, Faber O K, Binder C, Markussen, J, Heding L G, Naithani V K, Kuzuya H, Blix P, Horwitz D L, Rubenstein A H. Characterization of seven c-peptide antisera. *Diabetes* 27, Suppl 1: 170-177, 1978. The lower limit of sensitivity of the assay was 0.02 pmol/ml and the intraassay coefficient of variation averaged 6%. Glucagon was measured by using a commercially available radioimmunoassay kit (Biermann, Bad Nauheim, Germany) and the intraassay coefficient of variation averaged 8%. IR-GLP-1 was measured using the specific polyclonal antibody GA 1178 (Affinity Research, Nottingham, UK). It has 100% reactivity with GLP-1 (1-36) amide and the truncated GLP-1 (7-36) amide. Immunoreactive GLP-1 like material was extracted from plasma samples on C-18 cartridges employing acetonitrile for elution of the samples. The detection limit of the assay was 2 fmol/tube. The antiserum did not crossreact with GIP, pancreatic glucagon, glicentin, oxyntomodulin or GLP-2. Intra- and inter-assay coefficients of variation were 3.4% and 10.4%, respectively.

All results are expressed as mean±SEM. Data analysis was performed using the Statistical Analysis System (SAS Version 6 Edition, for Personal Computers, SAS Institute, Inc., Cary, N.C.). The significance of differences within the individual induced by GLP-1 infusion was determined using paired t tests. Differences were considered to be significant if $P<0.05$.

Standard kinetic parameters for C-peptide clearance adjusted for age, sex and body surface area were utilized, Van Cauter E, Mestrez, F, Sturis J, Polonsky K S. Estimation of insulin secretion rates from C-peptide levels: comparison of individual and standard kinetic parameters for C-peptide clearance. *Diabetes* 41:368-377, 1992. These parameters were used to derive, in each 15 minute interval between blood sampling, the ISR from the plasma C-peptide concentrations by deconvolution as previously described.

The diabetic subjects were treated with diet alone with the exception of one subject D07, who was previously treated with an oral hypoglycemic agent that was discontinued 4 weeks prior to the study. None of the diabetic patients had ever received insulin. All subjects were placed on a weight maintenance diet containing at least 200 g of carbohydrate per day for two weeks before the study.

Each subject was studied on three separate occasions. All studies were performed after a 12-hour overnight fast beginning at 0700 unless otherwise stated with subjects in the recumbent position. An intravenous catheter was placed in each forearm, one for blood sampling and one for administration of glucose and GLP-1 as needed. In all experiments, the arm containing the sampling catheter was maintained in a heating blanket to ensure arterialization of the venous sample. In the following examples, the GLP-1 was administered to the subjects in the GLP-1 (7-36) amide form.

Example 2 (Oral Glucose Tolerance Test)

Blood samples were drawn for the measurement of glucose, C-peptide, insulin, glucagon and GLP-1 at 30 minute intervals for 120 minutes after ingestion of 75 g glucose (Boehringer, Mannheim, Mannheim, Germany). Incremental areas under the curve (AUC) from 0 to 120 minutes were calculated for glucose, insulin, C-peptide, glucagon and GLP-1. The glucose concentrations were used to define the degree of glucose intolerance according to the criteria of the World Health Organization. The response of the IGT and NIDDM groups to oral glucose is set forth in Table 3.

Figure 1A:
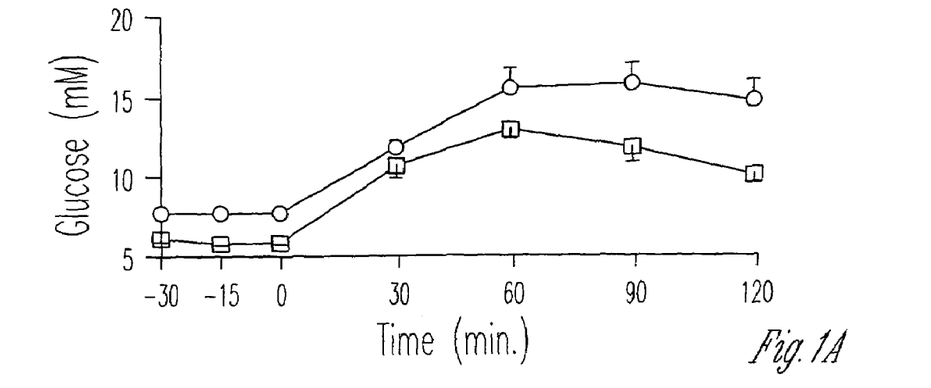
FIG. 1A shows mean glucose response.
Figure 1B:
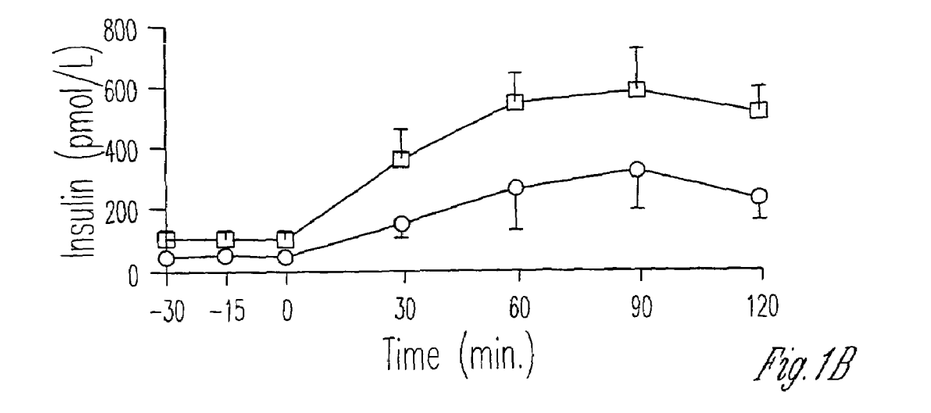
FIG. 1B shows insulin response.
Figure 1C:
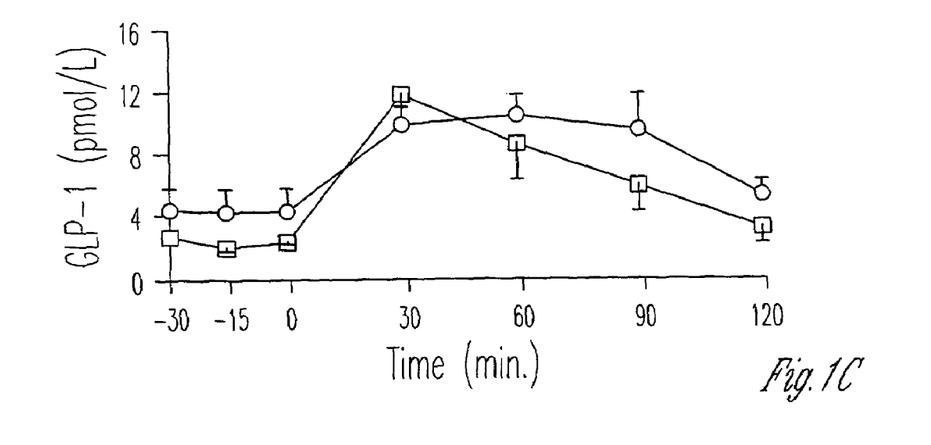
FIG. 1C shows GLP-1 response.

The glucose, insulin and GLP-1 responses of subjects to 75 mg of glucose is shown in FIG. 1. The AUC for glucose from 0 to 120 minutes was lower in the IGT group but the AUC for insulin, C-peptide, glucagon, and GLP-1 did not differ.

TABLE 3

Response to oral glucose

| 2 hr AUC | IGT n = 5 | NIDDM n = 5 |
|---|---|---|
| Glucose (mM. min/l) | 1290 ± 41 | 1628 ± 76* |
| Insulin (pmol. min/L) | 53,750 ± 10,648 | 26,083 ± 10,047 |
| C-peptide (pmol. min/L) | 293 ± 40 | 180 ± 48 |
| Glucagon (ng. min/L) | 8130 ± 1324 | 6858 ± 920 |
| GLP-1 (pmol. min/L) | 805 ± 141 | 983 ± 111 |

P < 0.05 for IGT vs NIDDM

Figure 2A:
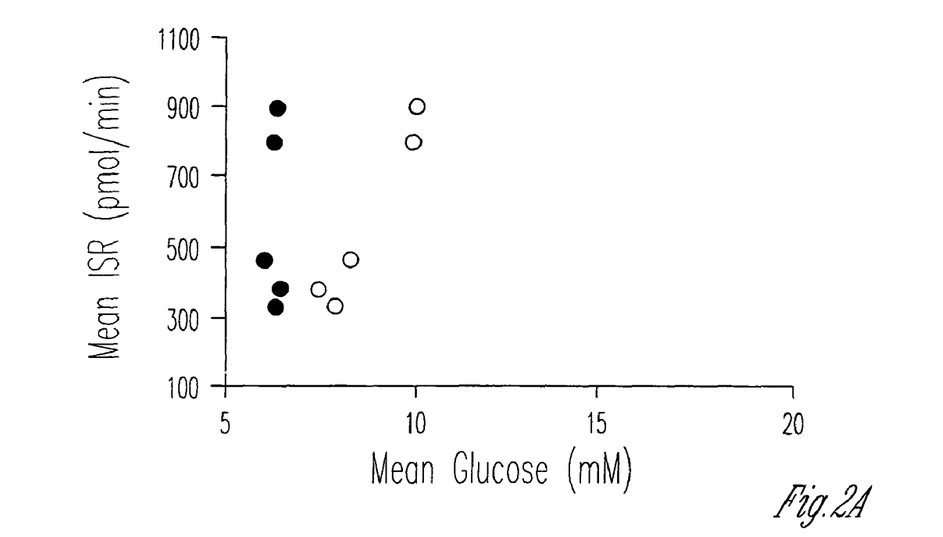
FIG. 2A shows the comparison in subjects with IGT.
Figure 2B:
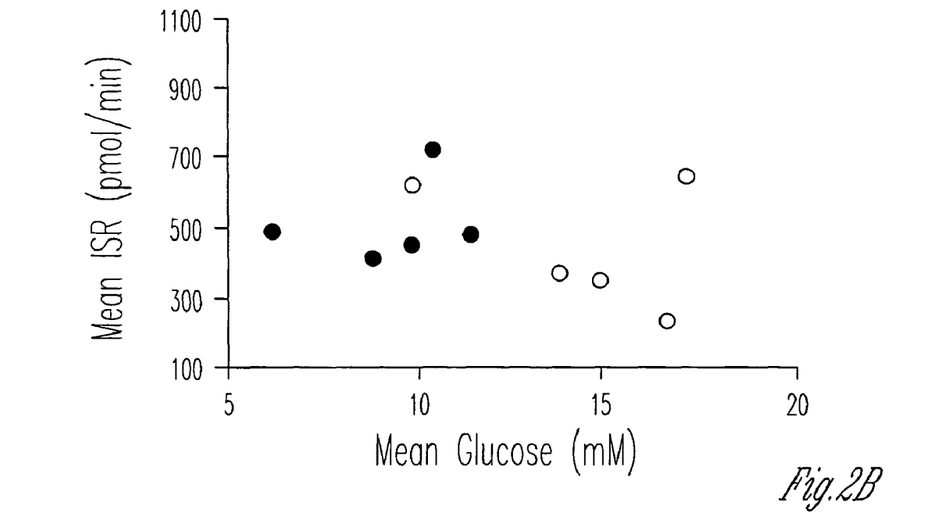
FIG. 2B shows the comparison in subjects with NIDDM.

When mean ISRs were plotted against mean glucose levels it was observed that GLP-1 caused a significant reduction in glucose levels without significantly altering the mean insulin secretion rates (FIG. 2).

Example 3 (Administration of an Oscillatory Glucose Infusion)

The peripheral administration of glucose in an oscillatory pattern results in regular oscillations in plasma glucose. In normal subjects, the β-cell is able to detect and respond to repetitive increases and decreases in glucose with parallel changes in insulin secretions. This adjustment of the insulin secretory oscillations to the glucose oscillations is termed entrainment. Lack of entrainment to glucose is an early manifestation of β-cell dysfunction in individuals with IGT and mild NIDDM.

We used a low-dose oscillatory glucose infusion protocol since it is a very sensitive test of the ability of the β-cell to sense and respond to small changes in plasma glucose concentrations. It tests the integrity of the feedback loop linking glucose and insulin secretion. A normal response requires an intact glucose sensing ability.

In order to determine whether the β-cells were able to detect and respond to oscillations of glucose, glucose was infused in an oscillatory pattern with a small volume of saline for 12 hours. The amplitude of the administered oscillations was 33% above and below the mean rate of 4 mg/kg/min and their periodicity was 144 minutes.

In order to establish the effect of GLP-1 on the ability of the β-cell to respond to oscillations of glucose, glucose was infused in the same manner and GLP-1 was infused at a constant rate of 0.4 pmol/kg/min for the entire 12 hours. Each study consisted of an initial 2-hour period (0700-0900) to allow a steady state to be achieved. This was followed by a subsequent period of 10 hours (0900-1900) during which time blood samples were drawn at 15 minute intervals for glucose, insulin, C-peptide, and glucagon and at 60 minute intervals for GLP-1.

Mean glucose levels were significantly lower in both groups during the GLP-1 infusion compared to saline, with an average drop of 2.4±0.6 mM in the IGT subjects (P<0.02) and 5.2±0.5 mM in the diabetics (P<0.0005). Despite this significant reduction in plasma glucose concentration, mean ISRs were not significantly different during the GLP-1 infusion compared to the saline infusion in both groups (Table 4).

TABLE 4

Mean glucose and ISR responses to 12 hour saline or GLP-1 infusion

| ID | Mean glucose 12 hour saline | Mean glucose 12 hour GLP-1 | Mean ISR 12 hour saline | Mean ISR 12 hour GLP-1 |
|---|---|---|---|---|
| IGT | | | | |
| D01 | 7.49 | 6.48 | 376.1 | 390.9 |
| D02 | 8.34 | 6.06 | 457.9 | 465.9 |
| D03 | 10.16 | 6.46 | 900.2 | 1042.7 |
| D04 | 7.90 | 6.36 | 328.5 | 365.9 |
| D05 | 10.06 | 6.37 | 798.0 | 1005.8 |
| Mean ± SEM | 8.79 ± 0.56 | 6.35 ± 0.08* | 572.1 ± 116.1 | 654.2 ± 152.1 |
| NIDDM | | | | |
| D06 | 16.73 | 11.53 | 232.3 | 477.7 |
| D07 | 17.28 | 10.51 | 640.3 | 715.4 |
| D08 | 9.94 | 6.24 | 615.6 | 487.7 |
| D09 | 13.95 | 8.84 | 366.5 | 412.5 |
| D10 | 15.05 | 9.90 | 346.2 | 448.9 |
| Mean ± SEM | 14.59 ± 1.3 | 9.40 ± 0.9* | 440.2 ± 80.1 | 508 ± 53.4 |

*P < 0.05, by paired t test, refers to comparison between saline and GLP-1 infusion.

Mean insulin levels were also maintained during the GLP-1 infusion compared to saline, increasing by 102±90 pmol/L; P=0.32 in subjects with IGT and increasing 7±12 pmol/L; P=0.56 in subjects with NIDDM. Mean glucagon levels were also not different during GLP-1 infusion compared to saline (39.3±5.4 pg/ml vs. 39.4±5.9 pg/ml; P=0.94) in subjects with IGT and (46.4±3.2 pg/ml vs. 42.8±5.4 pg/ml; P=0.4) in subjects with NIDDM. GLP-1 levels achieved during the GLP-1 infusion were 15.6±4.6 pmol/L compared to 2.0±0.8 pmol/L during saline infusion (P<0.001). These levels correspond to postprandial physiological levels.

Example 4 (Relationship Between Glucose and ISR in Individual Subjects with IGT)

Figure 3A:
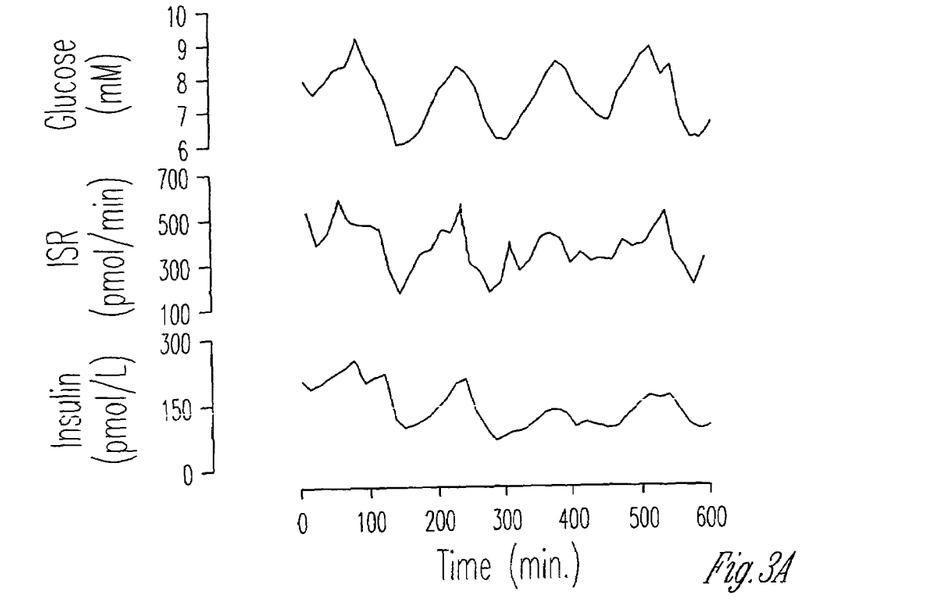
FIGS. 3A and 3C show the responses to saline infusion.
Figure 3B:
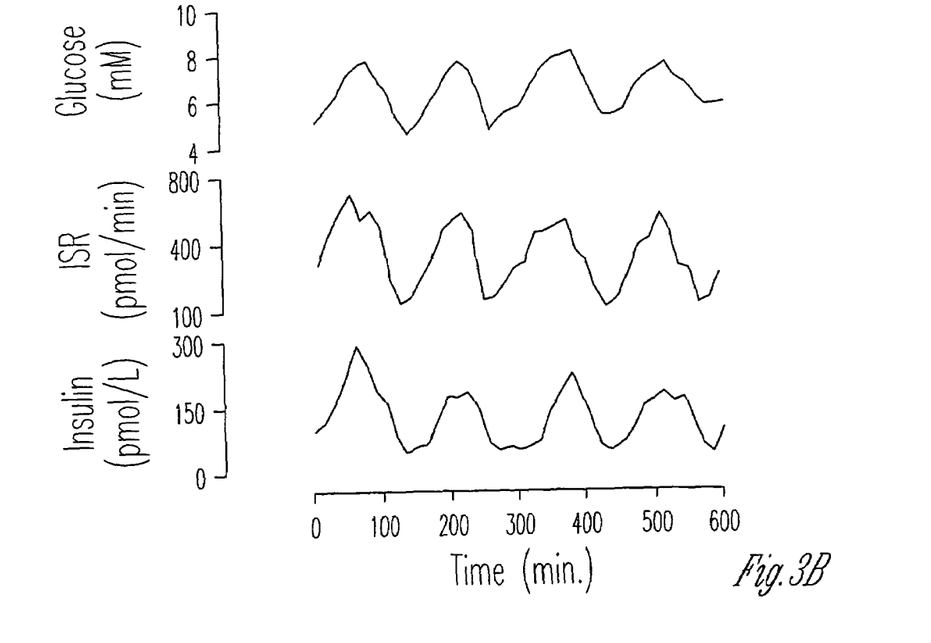
FIGS. 3B and 3D show the responses to GLP-1 infusion.
Figure 3C:
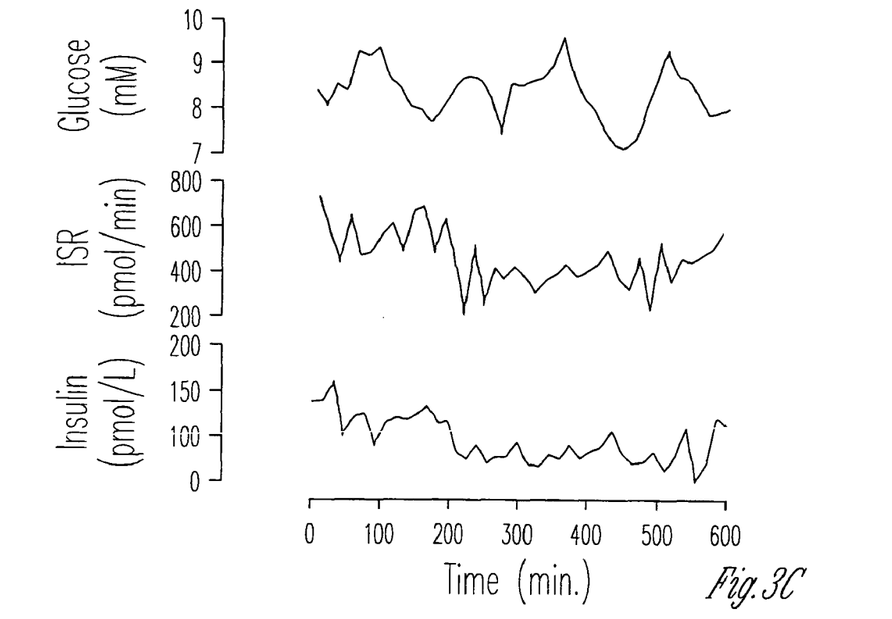
Figure 3D:
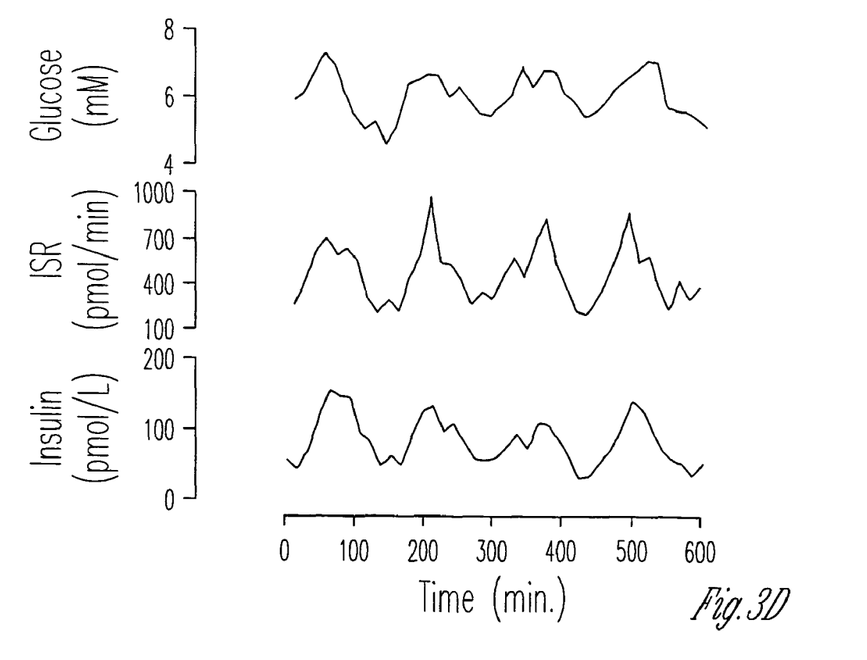

In normal subjects each pulse of glucose is tightly coupled to a pulse in ISR. This coupling has previously been shown to be defective in subjects with IGT. Profiles of glucose and ISR during the oscillatory glucose infusion with saline from representative subjects with IGT, D01 and D02, are shown in FIGS. 3A and 3C. These results demonstrate that in subjects with IGT, during saline infusion, there is loss of the tight coupling between glucose and ISR with many glucose independent oscillations in ISR. In the presence of physiological postprandial levels of GLP-1 (FIGS. 3B and 3D), the pattern of insulin secretory responses to glucose is improved in the subject with IGT, with each pulse in glucose followed by a pulse in ISR. Hence, GLP-1 improves the ability of the β-cell to entrain an exogenous glucose infusion in the subject with IGT.

Example 5 (Relationship Between Glucose and ISR in Individual Subjects with NIDDM)

Figure 4A:
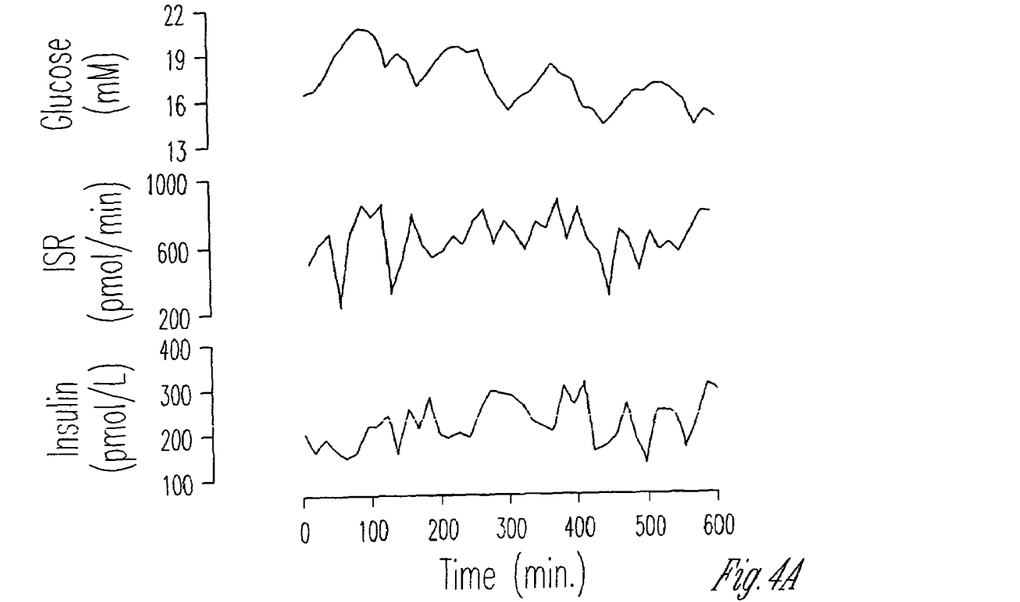
FIGS. 4A and 4C show the profiles during saline infusion.
Figure 4B:
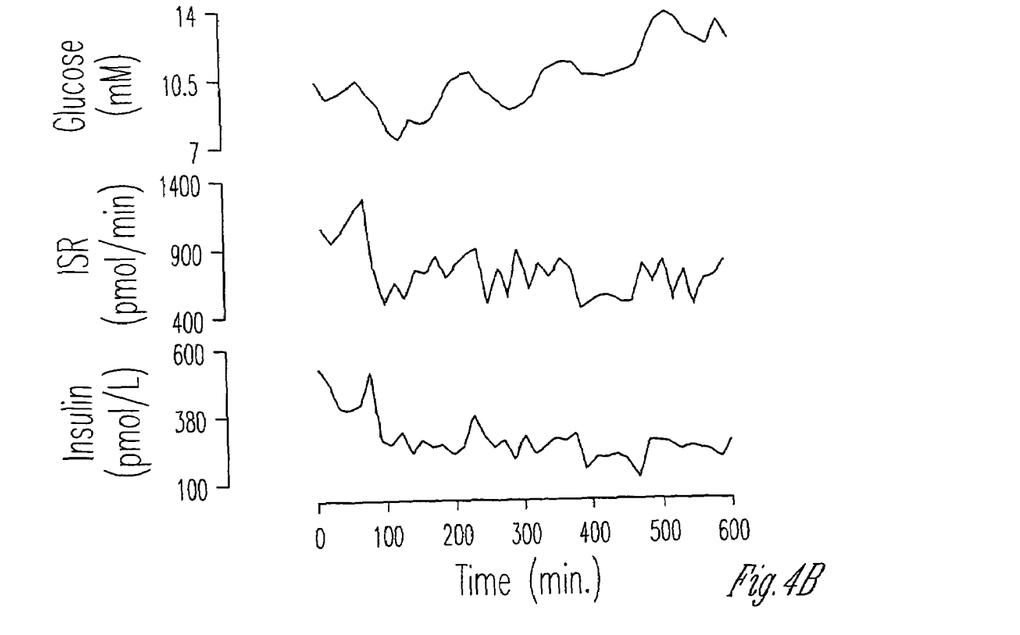
FIGS. 4B and 4D show the profiles during GLP-1 infusion.
Figure 4C:
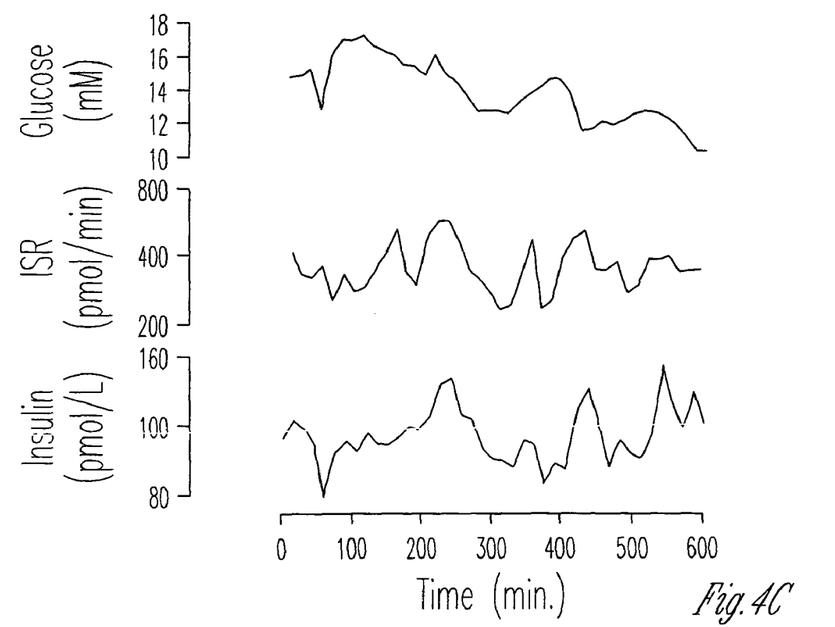
Figure 4D:
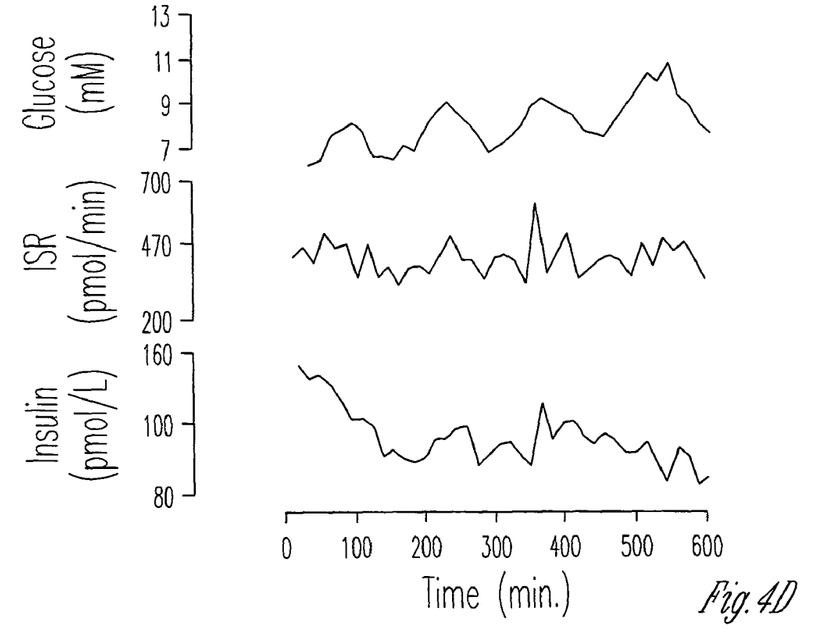

FIGS. 4A-4D show shows the profiles of glucose and ISR from two subject with NIDDM, D07 and D09. In marked contrast to subjects with IGT, despite the lowering of plasma glucose concentrations and the maintenance of ISR, the pattern of insulin secretory responses to glucose was not improved during the GLP-1 infusion (FIGS. 4B and 4D), with many glucose independent oscillations in ISR persisting. Profiles of glucose and ISR during the oscillatory glucose infusion with saline are shown in FIGS. 4A and 4C.

Example 6 (Effect of GLP-1 on Spectral Power in IGT and NIDDM)

To determine whether insulin secretion was entrained by glucose in individual subjects, the temporal profiles of insulin secretion were analyzed by spectral analysis. Spectral power analysis was used to evaluate the presence of tight coupling between oscillations in glucose and oscillations in ISR. This method evaluated the regularity of insulin secretory oscillations at a predetermined frequency. Spectral peaks correspond to the dominant periodicity and height of the peaks correspond to spectral power. Each spectrum was normalized assuming the total variance of each series to be 100% and was expressed as the normalized spectral power.

Figure 5A:
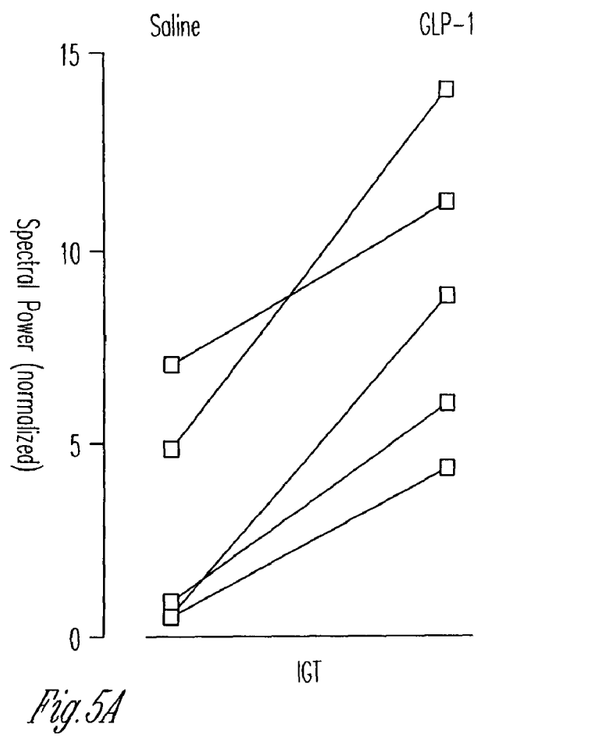
FIG. 5 provides a comparison of spectral analyses of insulin secretion in subjects during saline and GLP-1 infusions. Results shown on the left side of the spectral analysis are of subjects with IGT. Results shown on the right side of the spectral analysis are of subjects with NIDDM.
Figure 5B:
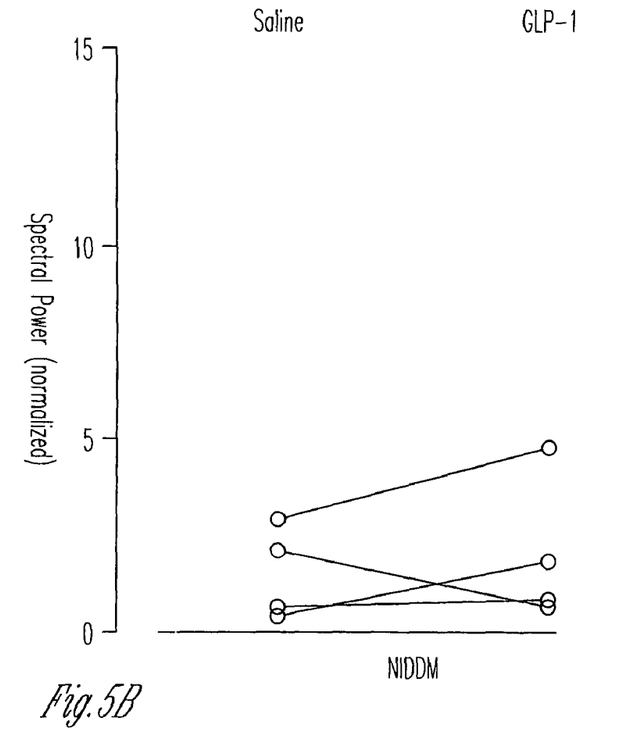
Figure 6A:
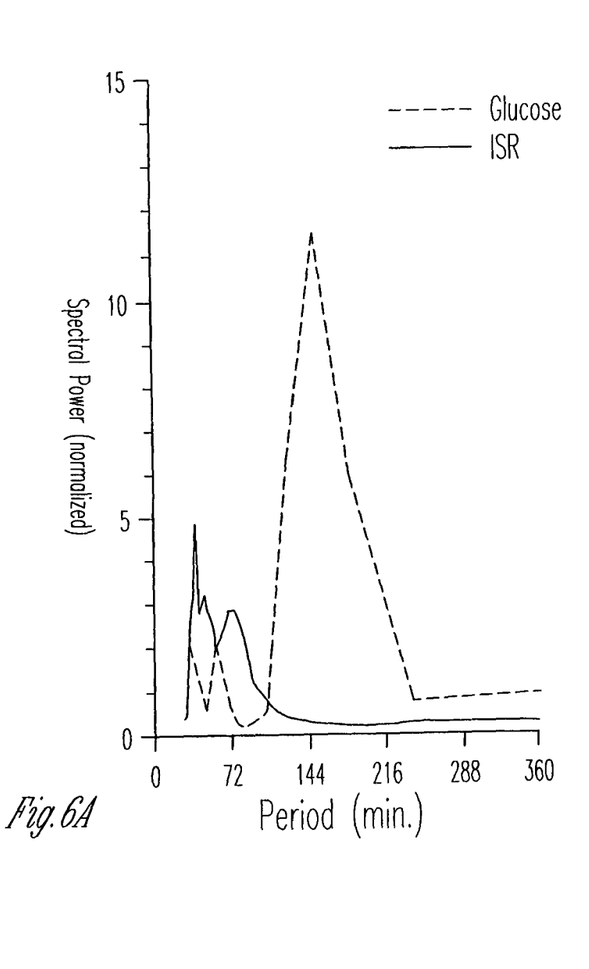
FIGS. 6A and 6B show a comparison of normalized spectral power during saline infusion (6A) and GLP-1 infusion (6B) in a subject with IGT (D02).
Figure 6B:
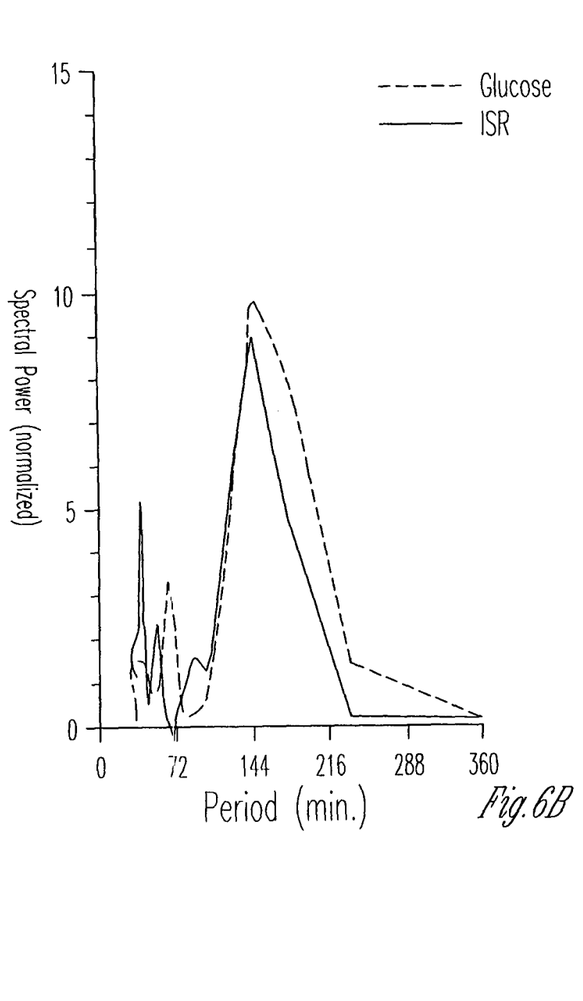
Figure 6C:
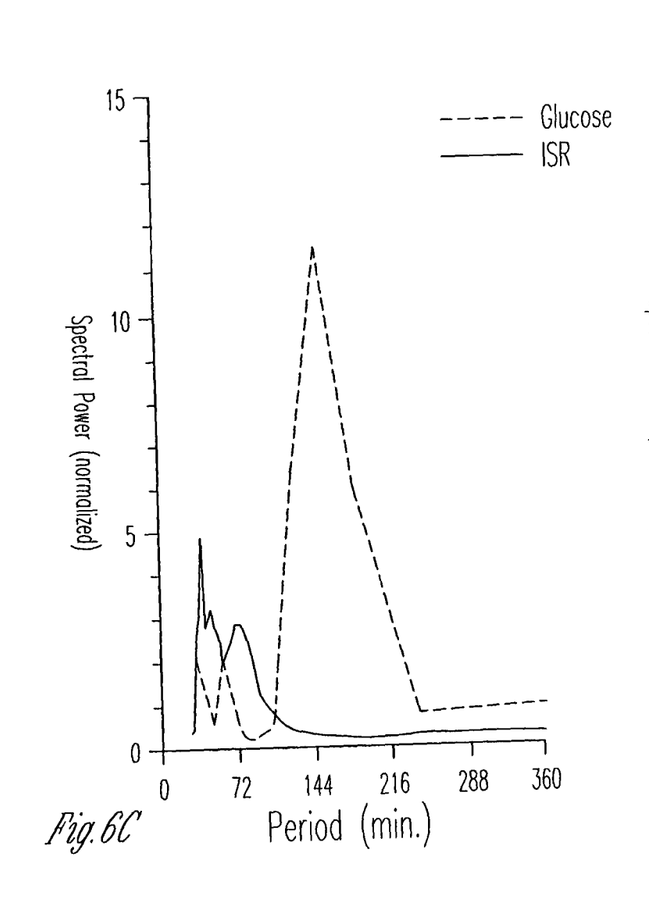
FIGS. 6C and 6D shows a comparison of normalized spectral power during saline infusion (6C) and GLP-1 infusion (6D) in a subject with NIDDM (D07).
Figure 6D:
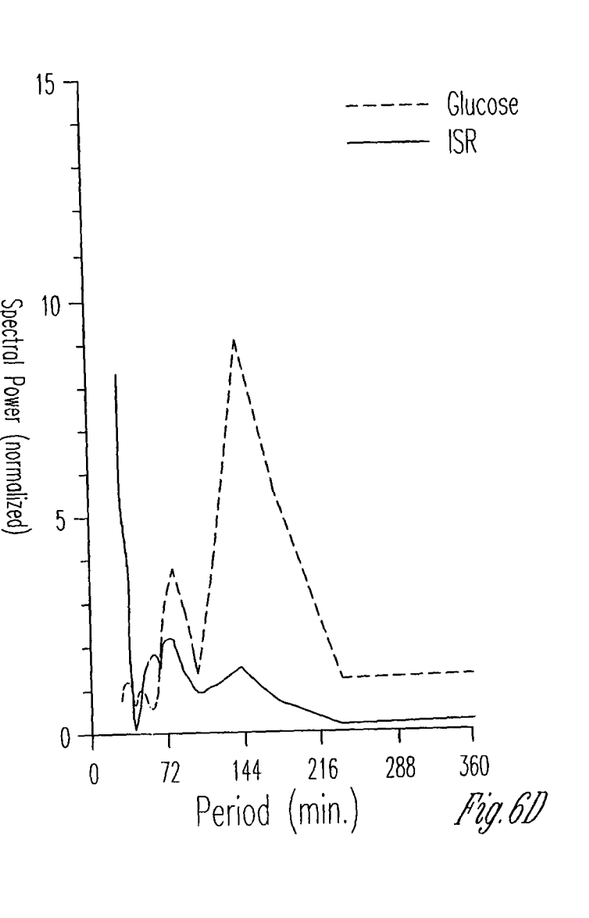

The mean normalized spectral power for glucose in subjects with IGT was 11.2±1.5 during saline infusion and 13.2±1.6 during GLP-1 infusion (P=0.19), and in subjects with NIDDM 6.5±1.8 during saline infusion and 9.8±0.7 during GLP-1 infusion (P=0.18). FIG. 5 clearly demonstrates that infusion of GLP-1 in subjects with IGT enhanced insulin secretory responses to the oscillations in plasma glucose, resulting in a greater degree of entrainment of insulin secretion to glucose. The effect was quantified by comparing the normalized spectral power of the insulin secretory profiles. Spectral power for ISR increased from 2.9±1.4 during saline infusion to 8.9±1.7 during GLP-1 infusion; (P<0.006) and was unchanged in subjects with NIDDM (1.1±0.5 to 1.5±0.8; P=0.6).

Spectral analysis of the oscillatory glucose profiles confirmed the existence of peaks in the plasma glucose spectra at 144 minutes corresponding to the period of exogenous glucose infusion. Individual power spectra for glucose and ISR in one subject with IGT (FIGS. 6A and 6B) and one subject with NIDDM (FIGS. 6C and 6D) during saline infusion and during GLP-1 infusion are shown in FIGS. 6A-6D. These correspond to the data shown in FIGS. 3C and 3D and FIGS. 4A and 4B. Spectral power increased from 0.6 to 8.9 in the IGT subject and was minimally changed from 0.28 to 1.51 in the subject in the subjects with NIDDM. Peaks in plasma glucose spectra occurred at 144 minutes. During saline infusion the dominant spectral peak for ISR did not occur at 144 minutes, but rather was at 0.2. Spectral power with GLP-1 infusion was 1.5.

During saline infusion there was poor entrainment (FIG. 3A) as the spectral power for ISR at 144 was 0.6. During GLP-1 infusion (FIG. 3B) the periodicity of the dominant spectral peak in ISR occurred at 144 minutes, demonstrating that GLP-1 caused the entrainment of the β-cell in this subject.

The mean value for normalized spectral power in historical weight matched control subjects (BMI 28.3) with normal glucose tolerance was 7.2±0.6(9).

The results of this study demonstrated that continuous infusion of physiological postprandial levels of GLP-1 reduced plasma glucose concentrations and stimulated insulin secretion in IGT and NIDDM subjects. Most importantly, GLP-1 restored the ability of the β-cell to sense and respond to plasma glucose in all IGT subjects (quantified by normalized spectral power), with a variable response in subjects who had already developed NIDDM.

The possible mechanisms via which P-cell function is improved by GLP-1 include upregulation of glucose-sensing elements, elimination of glucotoxicity, and improvement in insulin resistance. GLP-1 and glucose exert synergistic insulinotropic actions on β-cells, including stimulation of cyclic AMP formation, insulin secretion, insulin biosynthesis, and proinsulin gene expression.

These examples demonstrated that continuous infusion of physiological levels of GLP-1 reduced plasma glucose concentrations and stimulated insulin secretion in IGT and NIDDM subjects. Most importantly, GLP-1 restored the ability of the β-cell to sense and respond to small changes in plasma glucose concentrations in IGT subjects, with only a variable response in NIDDM subjects. In IGT subjects, we observed a significant increase in spectral power, a measure of β-cell function that does not rely on adjustment for changes in insulin sensitivity.

What is claimed is:

1. A method for treating an individual with impaired glucose tolerance who has not been diagnosed with non-insulin dependent diabetes mellitus (NIDDM), comprising: administering to said individual a composition comprising an exendin, thereby treating said impaired glucose tolerance.

2. The method of claim 1 wherein the exendin is exendin 3, SEQ ID NO:7.

3. The method of claim 1, wherein the exendin is exendin 4, SEQ ID NO:9.

4. The method of claim 1, wherein the step of administration is selected from the group consisting of intravenous, subcutaneous, intramuscular, intraperitoneal, injected depot with sustained release, deep lung insufflation with sustained release, buccal or patch.

5. The method of claim 1, wherein the exendin is administered in a range of 0.005 nmol/kg to 20 nmol/kg.

6. The method of claim 1, wherein said composition contains an amount of the exendin effective to enhance the regularity of insulin responses, or the amplitude thereof, in reaction to changes in plasma glucose.

7. The method of claim 1, wherein said composition contains an amount of the exendin effective to retard or arrest the loss of plasma glucose control or the development of non-insulin dependent diabetes mellitus.

8. The method of claim 1, wherein said composition contains an amount of the exendin effective to enhance a normalization of insulin secretory patterns in impaired glucose tolerance.

9. The method of claim 1, wherein said composition contains an amount of the exendin effective to reduce plasma insulin levels in an individual with impaired glucose tolerance.

10. The method of claim 1, wherein said composition contains an amount of the exendin-effective to reduce insulin resistance in an individual with impaired glucose tolerance.

11. A method for reducing a risk of a cardiovascular event due to impaired glucose tolerance, comprising:

administering to an individual at risk of a cardiovascular event due to impaired glucose tolerance a composition comprising an exendin-3 (SEQ ID NO:7), exendin-4 (SEQ ID NO: 9) or an agonist analog of exendin-3 or exendin-4, thereby reducing the risk of a cardiovascular event;

wherein said individual has not been diagnosed with non-insulin dependent diabetes mellitus (NIDDM).

12. The method of claim 11, wherein said composition contains an amount of the exendin-3, exendin-4 or agonist analog of exendin-3 or exendin-4, effective to enhance the regularity of insulin responses, or the amplitude thereof, in reaction to changes in plasma glucose.

13. A method for reducing a risk of a cerebrovascular event due to impaired glucose tolerance, comprising:

administering to an individual at risk of a cerebrovascular event due to impaired glucose tolerance a composition comprising exendin-3 (SEQ ID NO:7), exendin-4 (SEQ ID NO:9) or an agonist analog of exendin-3 or exendin-4, thereby reducing the risk of a cerebrovascular event;

wherein said individual has not been diagnosed with non-insulin dependent diabetes mellitus (NIDDM).

14. The method of claim 13, wherein said composition contains an amount of the exendin-3, exendin-4 or agonist analog of exendin-3 or exendin-4, effective to enhance the regularity of insulin responses, or the amplitude thereof, in reaction to changes in plasma glucose.

* * * * *